(12) United States Patent
Kamihara et al.

(10) Patent No.: US 9,383,376 B2
(45) Date of Patent: Jul. 5, 2016

(54) AUTOMATIC ANALYZER

(75) Inventors: Kumiko Kamihara, Mito (JP); Tomonori Mimura, Kasama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1061 days.

(21) Appl. No.: 13/133,655

(22) PCT Filed: Nov. 11, 2009

(86) PCT No.: PCT/JP2009/006000
§ 371 (c)(1),
(2), (4) Date: Aug. 23, 2011

(87) PCT Pub. No.: WO2010/067513
PCT Pub. Date: Jun. 17, 2010

(65) Prior Publication Data
US 2011/0301917 A1 Dec. 8, 2011

(30) Foreign Application Priority Data
Dec. 9, 2008 (JP) .................. 2008-312808

(51) Int. Cl.
*G06F 17/18* (2006.01)
*G01N 35/00* (2006.01)

(52) U.S. Cl.
CPC .......... *G01N 35/00693* (2013.01); *G06F 17/18* (2013.01)

(58) Field of Classification Search
CPC ........ G06F 17/18; G01N 35/00; G01N 21/00; G01N 31/00; G01N 33/00; B32B 27/04; B32B 5/02; B32B 27/12
USPC .................... 702/19, 179, 181, 185
See application file for complete search history.

(56) References Cited

U.S. PATENT DOCUMENTS

2007/0217949 A1* 9/2007 Mimura et al. ............... 422/63

FOREIGN PATENT DOCUMENTS

| JP | 2008-096218 A | 4/2008 |
| WO | WO-02/068963 A1 | 9/2002 |

OTHER PUBLICATIONS

Sekiguchi, Estimation of the Precision Based on the Basic Performance of Automatic Analyzer for Clinical Chemistry, 2007, JJCLA, vol. 32.*

(Continued)

*Primary Examiner* — Alexander Satanovsky
*Assistant Examiner* — Ivan Rabovianski
(74) *Attorney, Agent, or Firm* — Miles & Stockbridge, P.C.

(57) ABSTRACT

Abnormality causes are automatically identified during daily quality control, based on the focused consideration of complex uncertainty factors and, especially, of the causes of device-side abnormalities, the latter of which are often difficult to identify. The analyzer performance that affects measurement results can be estimated from analysis parameters and calibration results. Thus, uncertainty estimates are automatically calculated for each analysis item during quality control, and the estimates are compared with uncertainties obtained during actual QC sample measurement, thereby monitoring and evaluating the analyzer performance. Also, measurements are performed on QC samples of multiple concentrations that contain substances known to subject to particular influences such as those of the optical system, sample dispenser, and reagent dispenser, so that the causes of abnormalities can be identified. Uncertainty estimates calculated from the parameters set for the analysis items are compared with uncertainties obtained from the QC sample measurements.

9 Claims, 8 Drawing Sheets

(56) References Cited

OTHER PUBLICATIONS

Committee Report, Method for evaluating uncertainty in calibrators and QA samples (ver. 1.4), 2003, Clinical chemistry, vol. 32, 186-199.*

"Method for Evaluating Uncertainty in Calibrators and QA Samples (ver. 1.4)", Clinical Chemistry, 2003, vol. 32, pp. 186-199.

Satomi Kani, "Uncertainty in Daily Measured Values Propagated From a Standard System", Clinical Chemistry, 2007, vol. 36, sup. 1, pp. 151-154.

Mitsuo Sekiguch I, "Estimation of the Precision Based on the Basic Performances of Automatic Analyzer for Clinical Chemistry", Japanese Journal of Clinical Laboratory Automation, 2007, vol. 32, No. 1, pp. 3-11.

Japanese Journal of Clinical Laboratory Automation, Sep. 1, 2008, vol. 33, Suppl. 1, pp. 19-23.

Shigemi Hosogaya, "Global Standardized Evaluation Methods of Uncertainty in Measurement for Expression of Reliability of Clinical Test Data", Japanese Journal of Clinical Laboratory Automation, Nov. 1, 2005, vol. 30, No. 5, pp. 647-653.

* cited by examiner

<SAMPLE DISPENSER>

| AMOUNT OF SAMPLE DISPENSED | CV(%) |
|---|---|
| 1.0~2 | 1.0~1.5 |
| 3 | 0.7 |
| 4~5 | 0.4~0.5 |
| 6~20 | 0.3 |

<REAGENT DISPENSER>

| AMOUNT OF REAGENT DISPENSED | SD($\mu$L) | CV(%) |
|---|---|---|
| 350 | 0.21 | 0.06 |
| 300 | 0.21 | 0.07 |
| 200 | 0.3 | 0.15 |
| 100 | 0.24 | 0.24 |
| 50 | 0.145 | 0.29 |

$$\text{ERROR IN REAGENT DISPENSER} = \frac{\sqrt{(\text{STANDARD DEVIATION OF R1}) + (\text{STANDARD DEVIATION OF R2})}}{\text{LIQUID AMOUNT R1} + \text{LIQUID AMOUNT R2}} \times 100(\%)$$

<OPTICAL SYSTEM>

| PHOTOMETER NOISE ABSORBANCE | SD(Abs) |
|---|---|
| END-POINT METHOD | 0.001 |
| REACTION-RATE METHOD | 0.0001 |

$$\text{ERROR IN OPTICAL SYSTEM} = \frac{\text{PHOTOMETER NOISE ABSORBANCE}}{(\text{ABSORBANCE OF REACTED SAMPLE}) - (\text{BLANK ABSORBANCE})} \times 100(\%)$$

<RINSER>
ESTIMATED ERROR IS ASSUMED TO BE 1 $\mu$L.

$$\text{ERROR IN RINSER} = \frac{\sqrt{(\text{AMOUNT OF WATER LEFT})^2}}{\text{TOTAL REAGENT AMOUNT}(\mu L)} \times 100(\%)$$

<STIRRER>
ESTIMATED CARRY-OVER AMOUNT IS ASSUMED TO BE 1 $\mu$L.

$$\text{ERROR IN STIRRER} = \frac{\sqrt{(\text{WATER CARRY-OVER AMOUNT})^2}}{\text{TOTAL REAGENT AMOUNT}(\mu L)} \times 100(\%)$$

$$\text{COMBINED UNCERTAINTY ESTIMATE} = \sqrt{(\text{SAMPLE DISPENSER ERROR})^2 + (\text{REAGENT DISPENSER ERROR})^2 + (\text{OPTICAL ERROR})^2 + (\text{RINSER ERROR})^2 + (\text{STIRRER ERROR})^2}$$

SETTINGS

COMBINED UNCERTAINTY ESTIMATES

| ITEM | QC SAMPLE | SOURCES OF UNCERTAINTY | | | | | COMBINED EXPANDED UNCERTAINTY (%) | JUDGMENT CRITERION |
| --- | --- | --- | --- | --- | --- | --- | --- | --- |
| | | SAMPLE DISPENSER (%) | REAGENT DISPENSER (%) | OPTICAL SYSTEM (%) | RINSER (%) | STIRRER (%) | | |
| ALT | QC SAMPLE L | 0.50 | 0.19 | 5.99 | 0.70 | 0.70 | 6.10 | +2% |
| ALT | QC SAMPLE M | 0.50 | 0.19 | 0.60 | 0.70 | 0.70 | 1.27 | +1% |
| ALT | QC SAMPLE H | 0.50 | 0.19 | 0.30 | 0.70 | 0.70 | 1.16 | +0.5% |
| LD | QC SAMPLE L | 0.40 | 0.19 | 1.00 | 0.70 | 0.70 | 1.48 | +1% |
| LD | QC SAMPLE M | 0.40 | 0.19 | 0.10 | 0.70 | 0.70 | 1.09 | +0.5% |
| LD | QC SAMPLE H | 0.40 | 0.19 | 0.05 | 0.70 | 0.70 | 1.08 | +0.5% |
| TP | QC SAMPLE L | 1.50 | 0.15 | 0.54 | 0.50 | 0.50 | 1.75 | 1.5 TIMES |
| TP | QC SAMPLE M | 1.50 | 0.15 | 0.38 | 0.50 | 0.50 | 1.71 | 1.5 TIMES |
| TP | QC SAMPLE H | 1.50 | 0.15 | 0.19 | 0.50 | 0.50 | 1.68 | 1.5 TIMES |
| T-Cho | QC SAMPLE L | 1.50 | 0.20 | 0.37 | 0.50 | 0.50 | 1.71 | 1.5 TIMES |
| T-Cho | QC SAMPLE M | 1.50 | 0.20 | 0.08 | 0.50 | 0.50 | 1.67 | 1.5 TIMES |
| T-Cho | QC SAMPLE H | 1.50 | 0.20 | 0.04 | 0.50 | 0.50 | 1.67 | 1.5 TIMES |

EDIT DATA    DELETE    CLOSE

FIG. 7

SETTINGS / COMBINED UNCERTAINTY ESTIMATES / DATA EDIT

| ITEM | |
|---|---|
| ALT | QC SAMPLE L |
| ALT | QC SAMPLE M |
| ALT | QC SAMPLE H |
| LD | QC SAMPLE L |
| LD | QC SAMPLE M |
| LD | QC SAMPLE H |
| TP | QC SAMPLE L |
| TP | QC SAMPLE M |
| TP | QC SAMPLE H |
| T-Cho | QC SAMPLE L |
| T-Cho | QC SAMPLE M |
| T-Cho | QC SAMPLE H |

| | |
|---|---|
| SAMPLE DISPENSER (%) | 0.50 |
| REAGENT DISPENSER (%) | 0.19 |
| OPTICAL SYSTEM (%) | 5.99 |
| RINSER (%) | 0.70 |
| STIRRER (%) | 0.70 |
| COMBINED EXPANDED UNCERTAINTY (%) | 6.10 |
| JUDGMENT CRITERION | 1% |
| REFERENCE VALUE | 8.10% |

CHANGE →

| | |
|---|---|
| SAMPLE DISPENSER (%) | |
| REAGENT DISPENSER (%) | |
| OPTICAL SYSTEM (%) | |
| RINSER (%) | |
| STIRRER (%) | |
| COMBINED EXPANDED UNCERTAINTY (%) | |
| JUDGMENT CRITERION | |
| REFERENCE VALUE | |

[DEFAULT VALUES]   [CLOSE]

FIG. 8

RESULT / COMBINED UNCERTAINTY ESTIMATES

| ITEM | QC SAMPLE | LAST VALUE (%) | CURRENT VALUE (%) | COMBINED EXPANDED UNCERTAINTY (%) | REFERENCE VALUE (%) |
|---|---|---|---|---|---|
| ALT | QC SAMPLE L | 5.40 | 5.40 | 6.10 | 8.10 |
| | QC SAMPLE M | 1.00 | 1.00 | 1.27 | 2.27 |
| | QC SAMPLE H | 1.30 | 1.30 | 1.16 | 1.66 |
| LD | QC SAMPLE L | 1.30 | 1.30 | 1.48 | 2.48 |
| | QC SAMPLE M | 0.90 | 0.90 | 1.09 | 1.59 |
| | QC SAMPLE H | 1.20 | 1.20 | 1.08 | 1.58 |
| TP | QC SAMPLE L | 2.50 | 3.50 | 1.75 | 2.62 |
| | QC SAMPLE M | 2.40 | 3.50 | 1.71 | 2.56 |
| | QC SAMPLE H | 2.20 | 3.60 | 1.68 | 2.52 |
| T-Cho | QC SAMPLE L | 1.80 | 3.80 | 1.71 | 2.56 |
| | QC SAMPLE M | 1.95 | 3.30 | 1.67 | 2.50 |
| | QC SAMPLE H | 1.90 | 3.50 | 1.67 | 2.50 |

CAUTION: ABNORMAL CONTROL DATA
AN ABNORMALITY HAS BEEN FOUND IN THE SAMPLE DISPENSER.
RINSE OR REPLACE THE SAMPLE PROBE.

CHART    DELETE    CLOSE

FIG. 9

AUTOMATIC ANALYZER

This application is a National Stage Entry of PCT/JP2009/006000, filed on Nov. 11, 2009, which claims the benefit of Japanese Patent Application No. 2008-312803, filed on Dec. 9, 2008.

TECHNICAL FIELD

The present invention relates generally to automatic analyzers, such as clinical inspection apparatuses and the like, for performing quality control (or precision control) on themselves. Particularly, the invention relates to an automatic analyzer with means for estimating its abnormality causes based on calculated uncertainties.

BACKGROUND ART

In recent years, the need to evaluate the credibility of clinical assay has led to the development of ISO 15189 and the Guide to the Expression of Uncertainty in Measurement (GUM), creating the movement toward evaluation of the quality of inspection rooms and the precision of measurement results. In April 2008, the disease-specific health checkup program called "specific health checkup" was started based on studies of metabolic syndrome, with the ultimate goal of preventing lifestyle-related diseases such as diabetes and cardiovascular diseases. The program is designed to provide guidance on diet and lifestyle to those who exceed certain diagnostic criteria, but the guidance requires follow-ups, meaning that it has to be followed by several diagnoses. This means that if values measured during the diagnoses vary greatly from day to day or from institution to institution, it is difficult to relay on such fluctuating values to offer guidance. Thus, the same constant values have to be obtained at any testing institution, and more precise measurement is now needed. As for analytical reagents, a particular reagent has to be used for a particular analysis method, and reagent manufacturers are now obliged to disclose reagent-by-reagent uncertainties that are necessary for value calibration. Uncertainties are also required to be disclosed on an analyzer-by-analyzer basis. Non-Patent Documents 1 to 3 discuss such uncertainties.

Daily use of an automatic analyzer results in reduced lifetime of its lamp and wear of its dispenser syringe, which consequently increases uncertainties. Measured values may fluctuate also when the lamp or the syringe is replaced, due to a change in absorbance and the like. As for the lamp, syringe, and other consumable components, a commonly adopted approach is to keep track of the duration of use and replace those when they are overdue.

PRIOR ART LITERATURE

Non-Patent Documents

Non-Patent Document 1: Clinical chemistry, 2003, vol. 32, 186-199, Method for evaluating uncertainty in calibrators and QA samples (ver. 1.4)
Non-Patent Document 2: Japanese journal of clinical laboratory automation, vol. 32, no. 1, 19-23, A study for measurement uncertainty in routine tests using an automatic analyzer
Non-Patent Document 3: Clinical chemistry, 2007, vol. 36, sup. 1, 151-154, Uncertainty in daily measured values propagated from a standard system
Non-Patent Document 4: Japanese journal of clinical laboratory automation, vol. 32, no. 1, 3-11, Precision estimation based on the basic performance of an automated clinical chemistry analyzer

SUMMARY OF THE INVENTION

Problem to be Solved by the Invention

Measurement results obtained with an automatic analyzer are affected by the precision degrees of its components. However, it has been difficult to identify which component (the photometer, reagent dispenser, sample dispenser, or stirrer) affects the measurement results. Besides, the magnitude of such influence varies depending on items examined. Thus, it is quite time-consuming for a laboratory technologist to examine every piece of relevant data in an inspection room where he has to analyze many samples every day, so that he can determine which component is the cause of the influence.

In the present invention, standard blood serums of multiple concentrations are measured, and the measurement data are used to identify the causes of device-side abnormalities.

When measured values fluctuate greatly, one can determine that something is wrong in terms of quality control, whether it is based on reproducibility or accuracy as before or on uncertainty, which is now attracting attention. Uncertainty, however, is an index of technical credibility, and when uncertainty exceeds a clinically acceptable value, there is still no clear agreement on how to identify that cause or determine which factor was responsible—the device or the reagent. In the measurement of uncertainty, the uncertainty is caused by the combinations of multiple factors, such as the analyzer status including a maintenance status of the analyzer, the reagent, the quality control sample, and so forth. For this reason, it is considerably time-consuming and laborious for an ordinary laboratory technician to identify each such factor. This identification is often difficult, especially during routine inspection at the actual clinical site, and requires the inspection to halt to remove adverse factors; the result would be delay of the inspection or continuation of the inspection without proper precision control. As stated in the section of the background of the invention, studies have been conducted to improve the techniques of maintaining a certain level of precision and warning systems for imprecision alerts. However, in principle, the identification of adverse factors is left to the judgment of a laboratory technologist. Therefore, if it is necessary to achieve standardization of precision and measured values among clinical institutions as well as standardization of in-device precision, what matters is a unified perspective and a standardized judgment system.

Of all uncertainty factors, device-side abnormalities are most difficult to identify. Device-side factors that affect analysis precision include the sample dispenser, reagent dispenser, stirrer, photometer, reaction vessel, and so forth. As for the lamp, syringe, and other consumable components, uncertainty in data can be reduced to some extent by keeping track of the duration of use and replace those when they are overdue. In reality, however, the usable periods of those consumable components vary depending on their lot numbers and the status of use, and data precision decreases not suddenly but gradually after the usable periods have expired. For this reason, it is difficult to identify abnormal analyzer components using uncertainty in data.

Means for Solving the Problem

Figure 1:
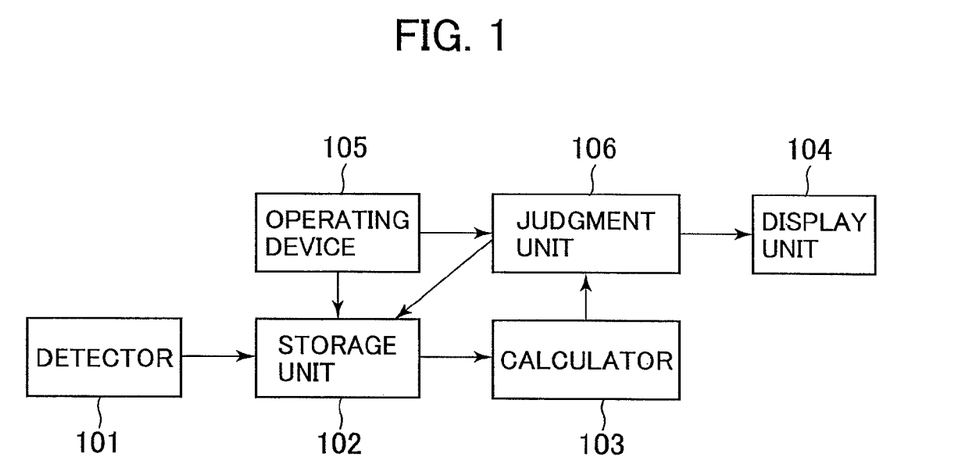
FIG. 1 is a schematic illustrating the basis configuration of an automatic analyzer according to the invention.

To solve the above problems, an automatic analyzer according to the present invention is configured as follows. As illustrated in FIG. 1, the analyzer includes: a detector 101 for outputting measurement data; a storage unit 102 (e.g., a hard disk) for storing the measurement data received from the detector 101, for storing and updating the data of multiple-level parameters to be measured, and for storing analysis item names, wavelengths measured, sample amounts, reagent amounts, analysis methods, and calibration results of the analysis items; a calculator 103 for calculating combined uncertainty estimates with the use of the analysis item names, wavelength measured, sample amounts, reagent amounts, analysis methods together with the K-factor, concentration, and absorbance of the calibration results and for calculating concentrations, standard deviations, coefficients of variation, dates, and the like from the data of each QC measurement (the storage unit 102 being adapted to store and update the data calculated by the calculator 103); a display unit 104 for displaying QC graphs and values; an operating device 105 (e.g., a keyboard and a CRT display) for setting reference values (i.e., limit values with which to judge whether measured values are abnormal) and the types and concentrations of samples; and a judgment unit 106 having multiple branch points in its algorithm logic for comparing calculated values against the reference values after QC sample measurement, thereby determining whether there is any abnormality or not, and if so, identifying the cause of the abnormality. The judgment result obtained by the judgment unit 106 is displayed on the display unit 104 with an alert sound.

Factors affecting the performance of an analyzer can be classified into two types. One is the factors that increase in influence in proportion to the concentrations of QC samples and regular samples to be measured. In this case, standard deviations increase in proportion to the concentrations of those samples. The influence of the factors of the type depends on the reaction system; hence, sample dispenser precision and reagent dispenser precision fall into this category. Another is the factors whose influence is not proportional to those concentrations. In this case, the standard deviations of measurement values are not proportional to concentration and remain almost constant. The factors that fall into this category are the photometer and rinse water carry-over, which are not subject to the influence of the reaction system such as reagents. As above, it is known that, depending on analysis items, the precision of measurement results is dependent on the sample amounts, the photometer, and the dispenser mechanisms. It is therefore possible to check analyzer precision and identify the cause of an abnormality by measuring particular items.

Effect of the Invention

If abnormalities of analyzer components can be automatically judged, it is possible, in the course of daily quality control, to judge analyzer abnormalities and deterioration of reagents. It is also possible to determine the proper replacement timing for consumable components. Moreover, when data is accumulated on a storage device, it is possible to examine why or in what cycle the analyzer escapes quality control, which would lead to prevention of a decrease in precision.

MODE FOR CARRYING OUT THE INVENTION

Embodiments of the present invention will now be described with reference to the accompanying drawings.

Embodiment 1

FIG. 1 illustrates the best mode of configuring an automatic analyzer according to the invention.

Quality control (or precision control) according to the invention involves first inputting information on multiple quality control (QC) samples, such as items to be examined and the like, using barcodes or an input device and then performing measurement. The measurement can be scheduled before and/or after daily inspections or in the middle of an inspection; it can also be programmed to start after a given number of samples have been measured or at a particular scheduled time. Before the measurement, necessary parameters are input from a screen, thereby extracting information such as 1) item names, 2) wavelengths measured, 3) sample amounts, 4) reagent amounts, and 5) analysis methods. Then, calibration is performed for the items to be examined, which is followed by calculations of uncertainties in the sample dispenser, reagent dispenser, rinser, stirrer, and photometer based on K-factor, absorbance, and the like. Thereafter, the square-root of sum of squares of those uncertainties is computed to obtain a combined uncertainty estimate for each of the items to be examined. Such combined uncertainty can be inputted from an operating device.

A detector 101 outputs measurement data to a storage unit 102 housed in a computer, where the data is recorded. Using this data, a calculator 103 computes averages, measurement ranges, standard deviations, coefficients of variation (CV), and so forth. The obtained values are stored on the storage unit 102 and can be displayed on a display unit 104 (e.g., computer screen). A judgment unit 106 compares the above-mentioned combined uncertainty estimates against uncertainties which are calculated by the calculator 103 after measurement of the QC samples, thereby judging whether there are value deviations or not, and if so, identifying the cause. The judgment unit 106 includes information necessary for this judgment. The identified cause can be displayed on the display unit 104 or notified with an alert sound.

Figure 2:
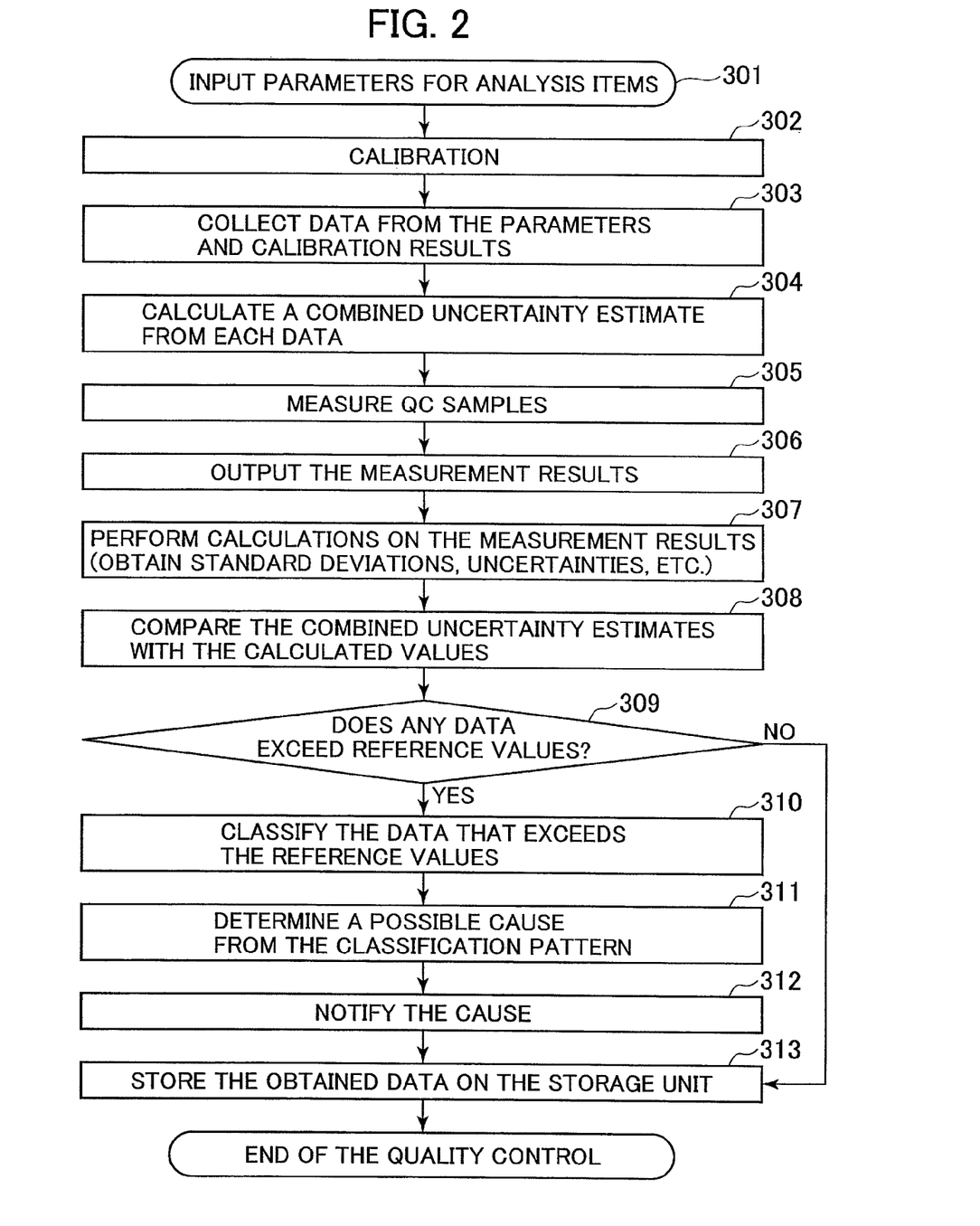
FIG. 2 is a flowchart of the process from QC sample measurement to value variation judgment.

FIG. 2 is a flowchart of the process from the QC measurement to the judgment.

In Step 301, the operating device (e.g., a computer-connected keyboard and a CRT display) is used to input and store the names and types of QC samples used, parameters for analysis items, desired reference values, and the like. In Step 302, calibration is performed for each of the analysis items. Then in Step 303, information such as 1) item names, 2) wavelengths measured, 3) sample amounts, 4) reagent amounts, and 5) analysis methods is extracted from the parameters. In addition, K-factor and absorbance, which are necessary for calculation of photometer noise, are extracted from the calibration result, thereby obtaining the uncertainty in the photometer. In Step 304, a combined uncertainty estimate is calculated for each of the analysis items based on all the information obtained in Step 303. Next in Step 305, the automatic analyzer performs measurement on the registered QC samples. This QC sample measurement is performed once or several times every day (e.g., after analyzer calibration or before, in the middle of, or after analysis of patients' samples). In Step 306, the detector outputs the obtained measurement data to the computer of the analyzer. Using the received data, the calculator computes averages, standard deviations, and the like in Step 307. In Step 308, the judgment unit then compares the combined uncertainty estimates (or desired reference values input) against the calculated standard deviations. By this comparison, the judgment unit identifies, on an item-by-item basis, those QC samples whose calculated standard deviations exceed the combined uncertainty estimates (or reference values). When there is no QC sample exceeding the reference value, it is determined that the precision of the analyzer is maintained, and the obtained data is stored in the storage unit at Step 312. When, on the other hand, there are one or more QC samples exceeding the reference value, their data is classified into categories which are characterized in advance by each item and include 1) optical system, 2) sample dispenser, 3) reagent dispenser, and so forth. In Step 310, the judgment unit 106 examines which items have value deviations from the reference values based on the classification pattern, thereby identify the analyzer uncertainty cause. Then in Step 311, the identified cause is displayed on the display unit 104 together with the associated item data. It is preferred that the display of the cause be accompanied by an alert sound because the display unit 104 may not be displaying the QC measurement window screen if this QC measurement is performed during an inspection. Finally, in Step 312, the data obtained thus far is stored on the storage unit 102 in the form of a database. The above constitutes the QC management of the present invention.

1. QC Samples

Examples of QC samples used for uncertainty measurement include standard blood serum, pooled blood serum, and control materials; they can be any as long as it contains a particular amount of the substance to be examined. Note however that QC samples of multiple concentrations are prepared for one analysis item. The concentration levels of those QC samples are within the measurement ranges of the reagent and analyzer. In the present embodiment, QC samples of three concentration levels are used. One is a QC sample L of a low concentration which is close to the lower limit of the reference range for normal values. Another is a QC sample M of a mid-level concentration which is close to the upper limit of the reference range. The other is a QC sample H of a high concentration which is twice or more times as high as the reference range. As above, it is preferred that those concentration levels be set at particular intervals.

2. Analysis Items

Analysis items may be any items which can be measured by the analyzer, and the factors effecting the measurement result of the items are known. It is preferred to select analysis items that need to be analyzed by the reaction-rate method and the end-point method. It is known that there exist more than 300 suitable analysis items. The following is a partial list of those analysis items: total protein (TP), albumin (ALB), lactase dehydrogenase (LD), aspartate aminotransferase (AST), alanine aminotransferase (ALT), alkaline phosphatase (ALP), amylase (AMY), pancreatic amylase (P-AMY), leucine aminopeptidase (LAP), gamma-glutamyl transpeptidase (γGT), cholinesterase (CHE), creatine kinase (CK), total cholesterol (T-Cho), neutral fat (TG), HDL cholesterol (HDL-C), LDL cholesterol (LDL-C), free fatty acids (FEA), urea nitrogen (UN), creatinine (CRE), uric acid (UA), glucose (Glu), hemoglobin A1c (HbA1c), lactic acid (LA), pyruvic acid (PA), total bilirubin (T-BIL), direct bilirubin (D-BIL), calcium (CA), sodium (NA), inorganic phosphorus (IP), serum iron (Fe), unsaturated iron binding capacity (UIBC), creatine kinase MB (CK-MB), phospholipids (PL), C-reactive protein (CRP), rheumatoid factor (RF), immunoglobulin G (IgG), immunoglobulin A (IgA), immunoglobulin M (IgM), complement component 3 (C3), complement component 4 (C4), antistreptolysin O (ASO), and so on. Of these substances, some are known to vary these low-concentration ranges, examples of which include aspartate aminotransferase (AST), alanine aminotransferase (ALT), alkaline phosphatase (ALP), total protein (TP), creatinine (CRE), and gamma-glutamyl transpeptidase (γGT). In the present invention, it is preferred to examine these substances.

3. Method for Calculating Combined Uncertainty Estimates

Analyzer uncertainties vary depending on the types of analyzers or from analyzer to analyzer, but can be estimated to some extent from factors that affect the precision of measurement data.

Figure 3:
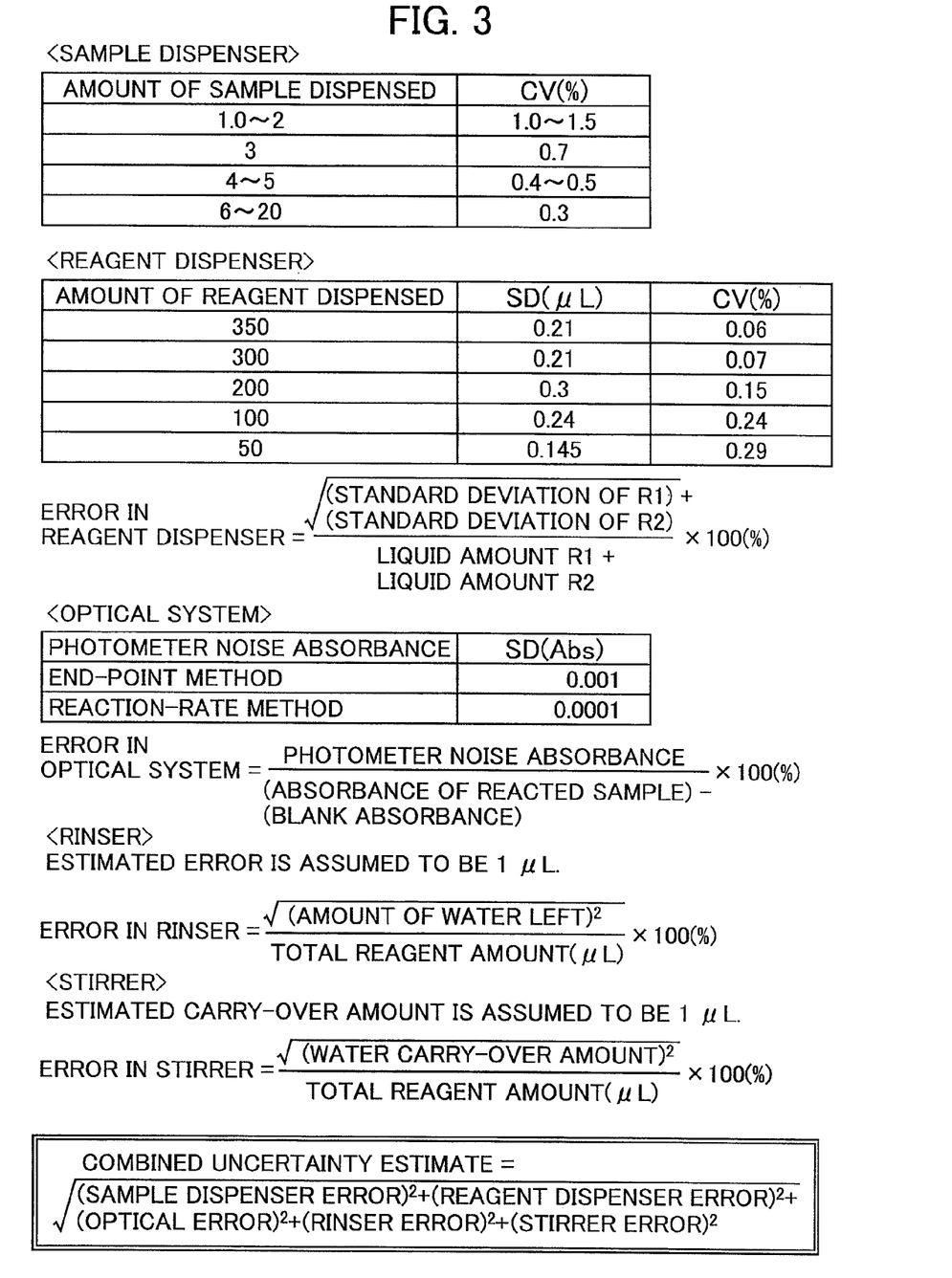
FIG. 3 shows methods for calculating the uncertainties of analyzer components and a combined uncertainty estimate.

Analyzer uncertainties are calculated from the performance data of some analyzer components. Uncertainties of the sample amount, reagent amount, photometer, rinser, and stirrer are determined based on the amounts dispensed, wavelengths measured, analysis methods, and the like. Thus, item-by-item uncertainty estimates of the sample amount, reagent amount, rinser, and stirrer are calculated from analysis parameters, and that of the photometer from calibration results. The storage unit 102 of the analyzer stores information on the uncertainties of those analyzer components such as those shown in FIG. 3, for example. After the input of analysis parameters for analysis items and subsequent calibration, the precision of each analyzer component is calculated to obtain item-by-item uncertainty estimates. The uncertainties of the analyzer components can be modified by the user conducting a performance evaluation during use of the analyzer and inputting the obtained value with the operating device 105 (e.g., a computer-connected keyboard and a CRT display), so that uncertainty estimates suitable for the analyzer used can be set.

4. Measurement Data Calculation

Figure 4:
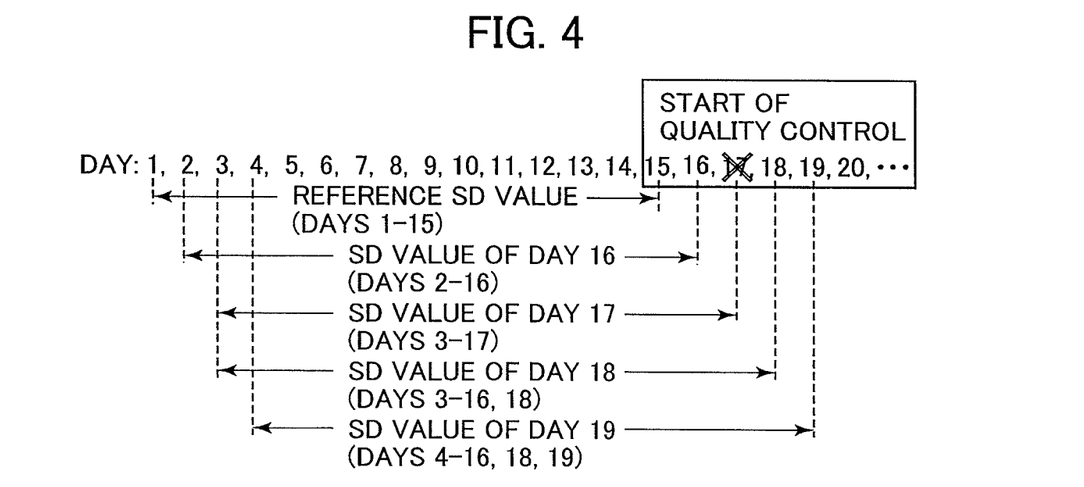
FIG. 4 illustrates an example of how to calculate SD values used in daily quality control.

Data uncertainty measurement becomes possible after the same QC samples are measured several times. In fact, when the within-run reproducibility of a reagent is measured, 20 to 30 independent data sets are used. In the case of within-day or between-day quality control as well, an increase in the number of measurements results in increased precision, but data uncertainty measurement can be performed when there are at least two data sets. Typically, the use of 15 or more independent data sets is recommended for the estimation of uncertainty in quality control; thus, the present embodiment is designed to use 15 data sets to perform data uncertainty measurement. To measure precision, averages, standard deviations, and the like can be used. FIG. 4 shows an example of quality control in which SD values are used with the sample size being 15 data sets. 15 days from the first measurement day are used for the accumulation of quality control data and for the calculation of SD values that can be used as reference values. The same QC samples are measured several times in a day, and the measured values are averaged to obtain the measurement values of that day. To make the sample size of reference values for judgment the same as that of measurement values for comparison, the data of past 15 days including the data of a measurement day is used. However, if there is any data, among measured values of the QC samples of three concentrations, that exceeds its associated reference value, that data will not be used because it will affect subsequent SD values. If, for example, the data obtained on the 17th day exceeds associated reference values, the SD values of the 18th day are calculated from the 15-day data sets that include the data of the 3rd to 16th and 18th days (excluding the data of the 17th day). Similarly, the SD values of the 19th day are calculated from the 15-day data sets that include the data of the 4th to 16th, 18th, and 19th days. When quality control measurement is performed several times in a day, it is preferred to use past 15 data sets. Past data is stored for recalculation. The number of days can be specified.

5. Settings of Reference Values

It is extremely rare for an analyzer to obtain the same measurement data and the same uncertainties every day. Even slight variations of measurement data result in changes in the values of uncertainties. Accordingly, it is important to determine whether the range of an uncertainty fluctuation is within or out of an acceptable range, rather than whether there are fluctuations in the values of uncertainties.

To evaluate uncertainty, a combined uncertainty is commonly multiplied by the coverage factor K to obtain an expanded uncertainty, thereby obtaining the confidence level of the combined uncertainty. A confidence level is used to define the dispersion of a normal distribution, and the same concept applies here. When the value of K is 1, 2, and 3, the resultant confidence levels are 68%, 95%, and 99.7%, respectively, and the K value of 2 is most commonly used to calculate an expanded uncertainty. When the confidence level is set to too high a value in actual measurement, this only increases the possibility that value fluctuations not resulting from an abnormality may be out of the confidence interval, which may impede inspection tasks. Because demanded precision varies from institution to institution or from item to item, the automatic analyzer of the present invention allows a laboratory technologist to set reference values freely. Reference values can be input or modified before and after each QC sample measurement.

The automatic analyzer is designed to store in advance the uncertainty values of its relevant components obtained through experiments and the associated conditions used for obtaining the uncertainties. However, because device-side uncertainty varies from analyzer to analyzer, the stored uncertainty values can be reset during an analyzer performance evaluation before shipment, at the time of installation by the user, or after maintenance. To set proper reference values, while the analyzer is stable in terms of its measurement process, an N number of standard blood serums of several concentrations are first measured ever day, and the measurement is continued for a K number of days to collect data. During the measurement, it is preferred to use QC samples and reagents of the same lot numbers. The collected data is then used to calculate averages, standard deviations, coefficients of variation, and so forth. Those values are subjected to X times multiplication or addition/subtraction of Z % to calculate reference values. The reference values can be fixed values or variables, the latter of which requires an increase in sample size by repeating QC sample measurement.

In the present embodiment, a combined uncertainty estimate is multiplied by a coverage factor K of 2 to obtain an expanded uncertainty, which serves as an acceptable limit range of device abnormalities.

6. Display Method

Figure 6:
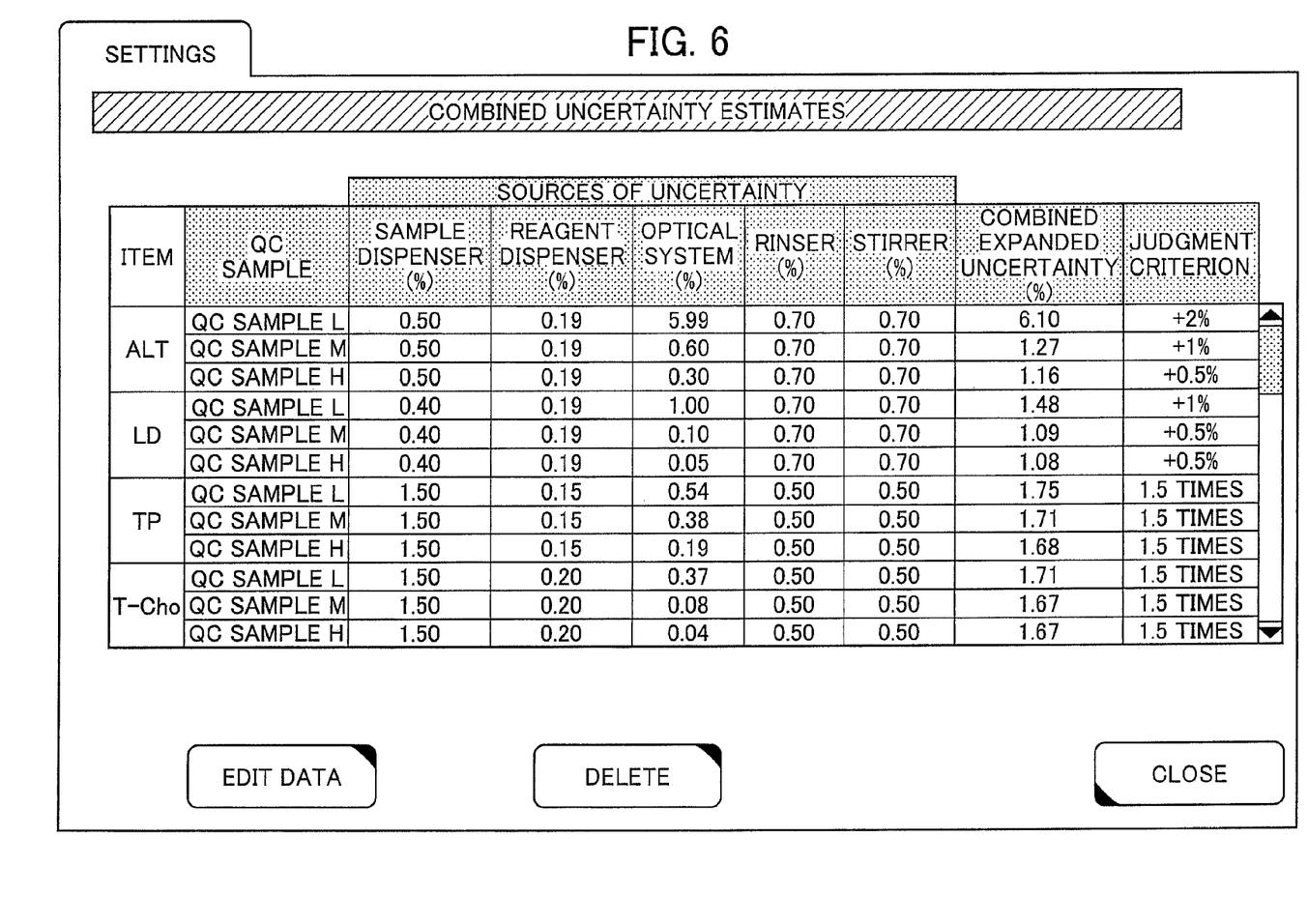
FIG. 6 is an exemplary screen for setting values for factors associated with combined uncertainty estimates.
Figure 7:
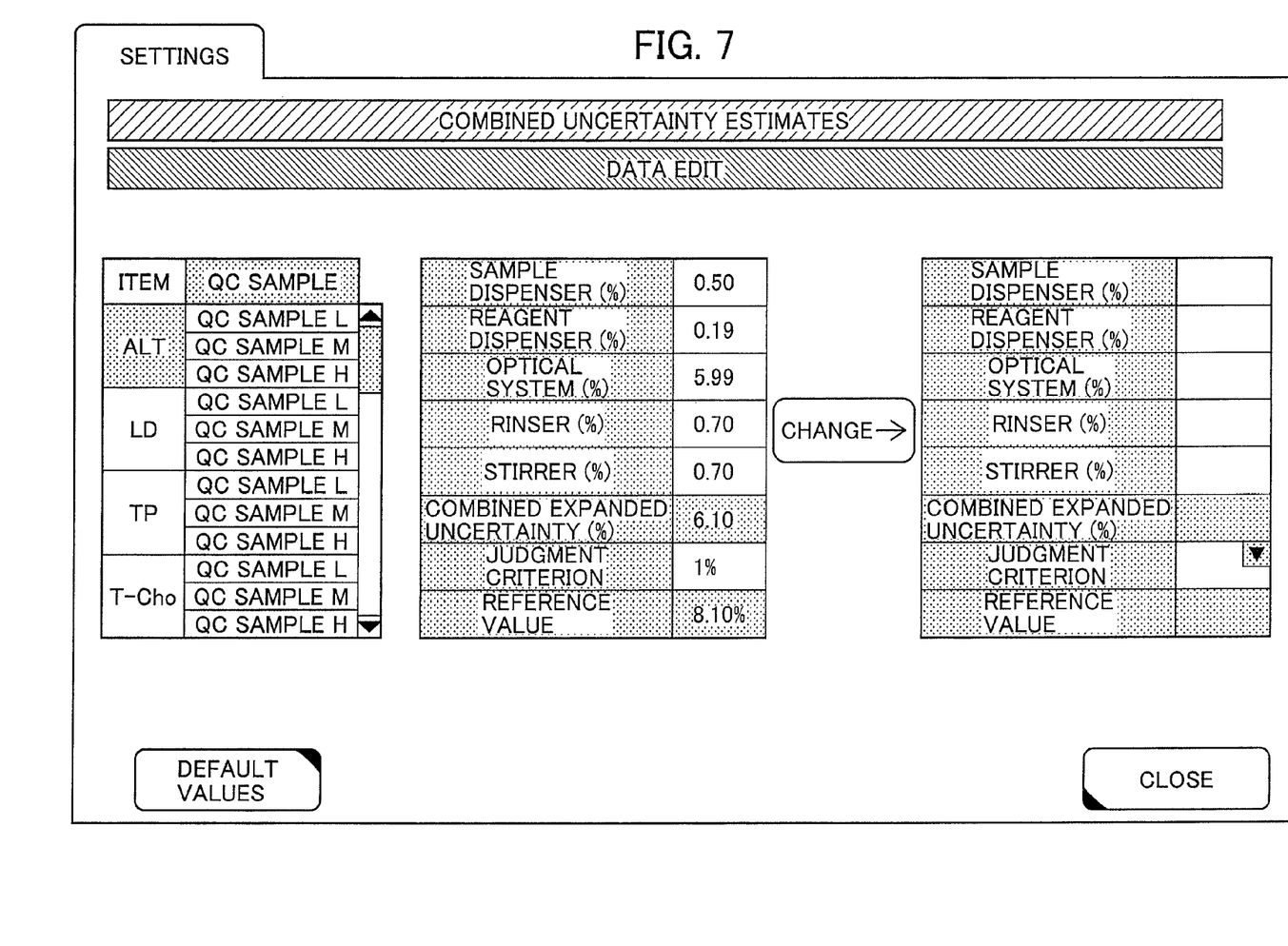
FIG. 7 is an exemplary data edit screen for combined uncertainty estimates.

When parameters are input for analysis items used for uncertainty calculation, the combined uncertainty estimates of analyzer components are calculated, and the display unit 104 displays the result as illustrated in FIG. 6. On this screen, the user can know how much the combined uncertainty estimates will be on an item-by-item basis. From this screen, the user can also jump to a data edit screen such as the one illustrated in FIG. 7. On this screen, the user can freely input analyzer component uncertainties or reference values with the use of the operating device 105.

Figure 8:
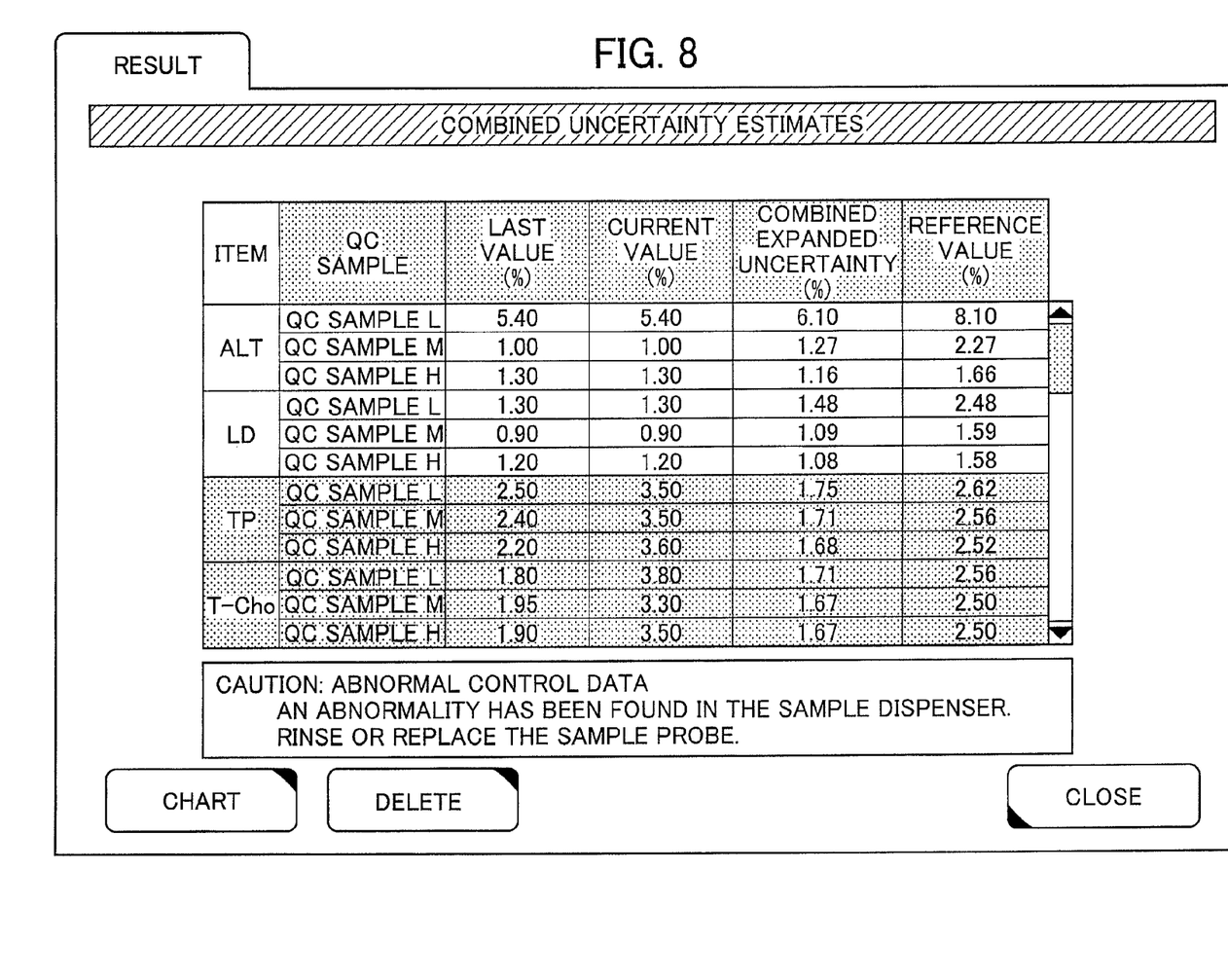
FIG. 8 is an exemplary measurement result screen for combined uncertainty estimates.

After the QC samples are measured on an item-by-item basis, the display unit 104 displays the result of the QC measurement (i.e., the estimation result of combined uncertainties) such as the one illustrated in FIG. 8. The values of the uncertainties obtained in this QC measurement are displayed together with the values obtained in the last QC measurement, so that the user can compare them. As illustrated in FIG. 8, the combined uncertainty estimates and reference values are also displayed side-by-side for comparison. It is preferred that the cells of those items that exceed reference values be colored to attract the user's attention.

It is also preferred for the screen to show an alert message to notify the user of the causes of data abnormalities when there are items that exceed reference values, together with how to rectify the abnormalities.

It is also possible for a QC screen to display item-by-item uncertainty estimates together with measured values in the form of a graph.

Figure 5:
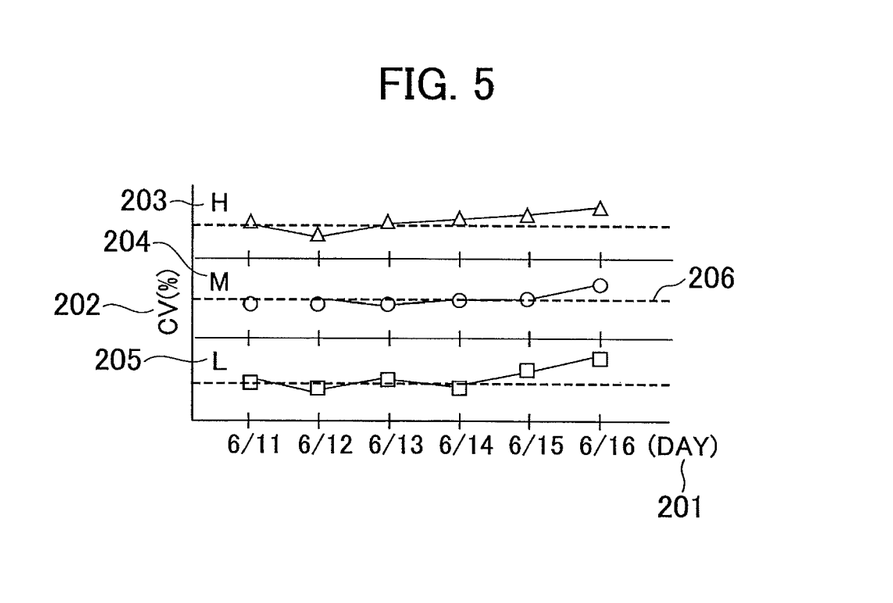
FIG. 5 is an example of quality control display.
Figure 9:
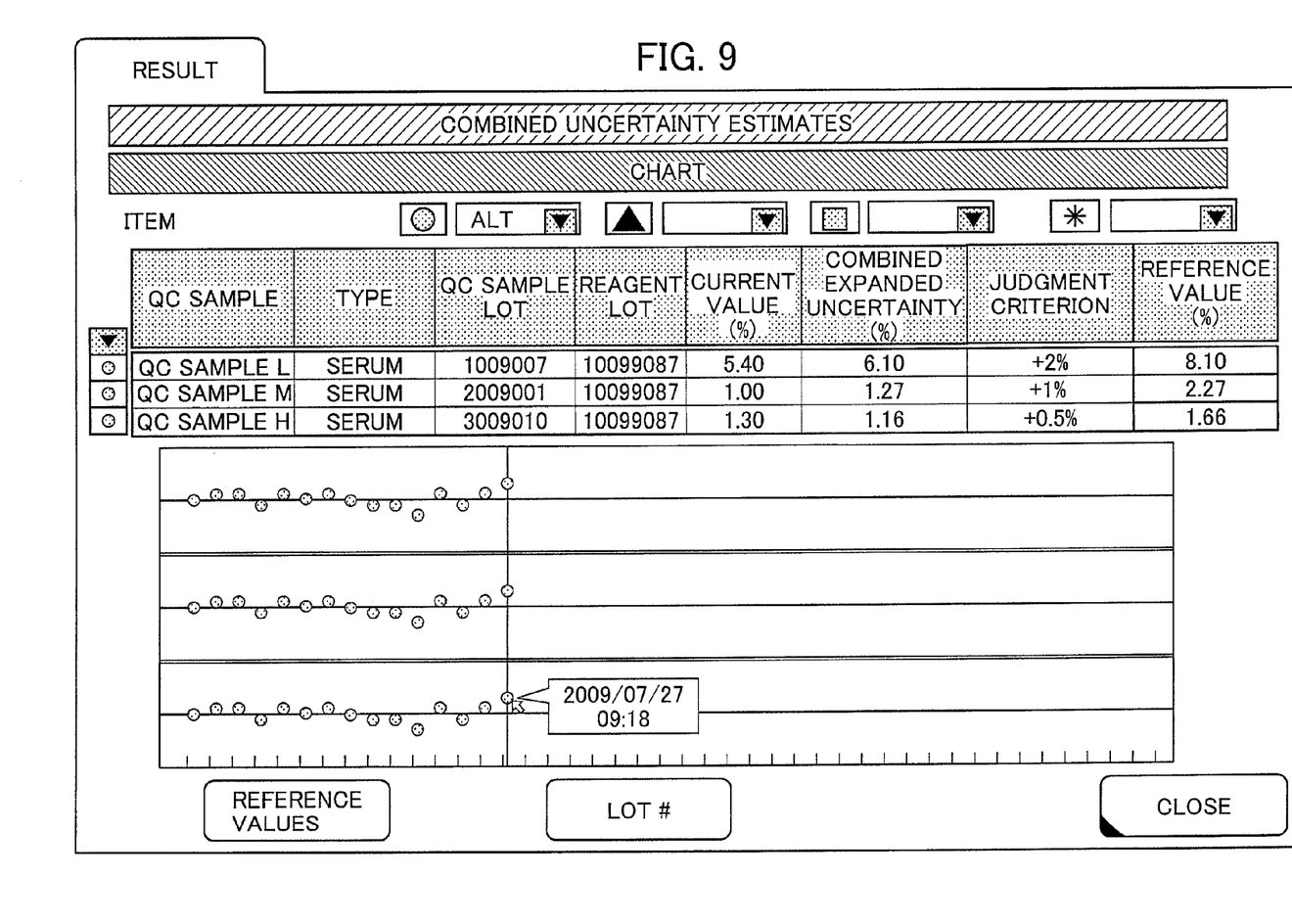
FIG. 9 is a graph illustrating day-to-day fluctuations of combined uncertainty estimates.

An example is illustrated in the QC graph of FIG. 5 in which, similar to typical QC graphs, the horizontal axis 201 represents dates, and the vertical axis 202 represents coefficients of variation CV %. Basically, such a graph is prepared for each analysis item, and QC graphs for concentration are displayed independently for each concentration or displayed on a single screen in a superimposed manner. Alternatively, as in FIG. 5, a single graph can display the values of the QC sample H (203), the QC sample M (204), and the QC sample L (205) in a vertically aligned manner. FIG. 9 illustrates how such a QC graph is displayed on a screen. As illustrated in FIG. 9, the values of the QC samples L, M, and H are displayed in a vertically aligned manner with the horizontal axis representing temporal sequence. It is also possible to display the values of the QC samples in a superimposed manner on an item-by-item basis, so that the user can view such a graph when the cause of an abnormality is attributed to a change in the lot numbers of the QC samples. It is preferred that the selection of a particular point of a QC graph trigger the display of measurement time/date or other detailed data.

Instead of using QC graphs, it is also possible to display data in a tabular format on a date-by-date basis, and different colors can be applied to the cells so that the user can see which analysis item is subject to the influence of what analyzer component. Those values that exceed uncertainty estimates or reference values can be displayed in red.

7. Judgment Method

As stated in Non-Patent Document 1, particular analyzer components among 1) optical system, 2) sample dispenser, 3) reagent dispenser, and 4) rinser are known to greatly affect measurement results, depending on the substance analyzed.

As for the optical system, for example, the noise influence of the halogen lamp used as the light source becomes greater as the light intensity of the lamp decreases due to a decrease in lifetime. This noise influence varies depending on the wavelengths measured. For instance, analysis items are more subject to optical influence when wavelengths in the ultraviolet and near-infrared ranges (e.g., main wavelength of 340 nm/sub-wavelength of 405 nm) are measured. In contrast, when wavelengths in the visible range (e.g., main wavelength of 405 nm/sub-wavelength of 505 nm) are measured, the noise influence is smaller, and analysis items are less subject to optical influence. Thus, analysis items suitable for detecting abnormalities of the optical system are those items that require the measurement of the former wavelength ranges. Further, substances measured under the enzyme reaction-rate method are more susceptible to the noise influence as the QC samples that contain those substances increase in concentration.

As for the sample dispenser, analysis items are more subject to its influence when the QC samples that contain the analysis items are dispensed in smaller amounts. Accordingly, it is preferred that the QC sample dispensing amount of the analyzer be set to the smallest possible value while the amount may vary from analyzer to analyzer. Enzyme-related items that have a narrower range of acceptable measurement values require larger amounts of QC samples and are thus less subject to the influence of the sample dispenser when the QC samples are low in concentration. In contrast, smaller QC sample dispensing amounts are often set for items that have a wider range of acceptable measurement values, especially those items that involve the end-point method; thus, such items are more subject to the precision of the sample dispenser. As the concentration of a QC sample increases, the sample dispenser exerts a greater influence on its associated analysis items. Also, ALP and other highly-sensitive items are greatly influenced by value variations of the sample dispenser. With regard to the reagent dispenser, most analysis items are not subject to its precision because the reagent dispensing amount is often set to a high value. When a reagent containing an excessive amount of a substrate is used (such as one involving the substrate method), analysis items are less subject to the precision of the reagent dispenser. The above being stated, analysis items suitable for analyzer abnormality detection are shown in Table 1.

TABLE 1

Example of analysis items suitable for device abnormality judgment

| Item | Wavelengths (nm) | Analysis Method | | Influential factor |
|---|---|---|---|---|
| CK | 340/405 | Reaction rate | Enzyme | Optical system |
| CK-MB | 340/405 | Reaction rate | Enzyme | Optical system |
| Glu | 340/405 | Reaction rate | Enzyme | Optical system |
| ALT | 340/405 | Reaction rate | Enzyme | Optical system |
| AST | 340/405 | Reaction rate | Enzyme | Optical system |
| LD | 340/405 | Reaction rate | Enzyme | Optical system |
| UN | 340/405 | Reaction rate | Enzyme | Sample dispenser & optical system |
| Mg | 340/405 | Reaction rate | Enzyme | Optical system |
| ALP | 405/505 | Reaction rate | Enzyme | Sample dispenser |
| TP | 546/700 | 1-point end | Biuret | Sample dispenser |
| T-Cho | 600/700 | 2-point end | Enzyme | Sample dispenser |
| UA | 600/700 | 2-point end | Enzyme | Sample dispenser |
| CRE | 570/700 | 2-point end | Enzyme | Sample dispenser |

Some of the above analysis items are used in a combined manner to perform QC measurement, and the measurement result is used to judge analyzer abnormalities.

Measurement Example 1

The QC samples L, M, and H were measured in terms of ALT and LD, which are subject to the precision of the optical system, and TP and T-Cho, which are subject to the precision of the sample dispenser. Table 2 below shows the analysis parameters used such as the amounts of the samples dispensed, the wavelengths measured, the amounts of reagents dispensed (R1 and R2), and the analysis methods.

TABLE 2

Input data of Measurement Example 1

| Item | Optical system | | Sample dispenser | |
|---|---|---|---|---|
| | ALT | LD | TP | T-Cho |
| Sample amount dispensed | 5 | 4 | 1.5 | 3 |
| Wavelengths | 340/546 | 340/405 | 546/700 | 600/800 |
| Reagent amount dispensed (R1) | 100 | 100 | 200 | 150 |
| Reagent amount dispensed (R2) | 50 | 50 | — | 50 |
| Analysis method | Reaction-rate A | Reaction-rate A | 1-point end | 2-point end |

After the input of the parameters and subsequent calibration, the following analyzer component uncertainties were obtained as shown in Table 3 below.

TABLE 3

Uncertainties of analyzer components and combined uncertainty estimates in Measurement Example 1

| | Item/Sample | Analyzer component | | | | | Combined uncertainty estimate (%) |
|---|---|---|---|---|---|---|---|
| | | Sample dispenser (%) | Reagent dispenser (%) | Optical system (%) | Rinser (%) | Stirrer (%) | |
| ALT | QC sample L | 0.50 | 0.19 | 5.99 | 0.70 | 0.70 | 6.10 |
| | QC sample M | 0.50 | 0.19 | 0.60 | 0.70 | 0.70 | 1.27 |
| | QC sample H | 0.50 | 0.19 | 0.30 | 0.70 | 0.70 | 1.16 |

TABLE 3-continued

Uncertainties of analyzer components and combined uncertainty estimates in Measurement Example 1

|  | | Analyzer component | | | | | Combined uncertainty estimate (%) |
|---|---|---|---|---|---|---|---|
| | Item/Sample | Sample dispenser (%) | Reagent dispenser (%) | Optical system (%) | Rinser (%) | Stirrer (%) | |
| LD | QC sample L | 0.40 | 0.19 | 1.00 | 0.70 | 0.70 | 1.48 |
| | QC sample M | 0.40 | 0.19 | 0.10 | 0.70 | 0.70 | 1.09 |
| | QC sample H | 0.40 | 0.19 | 0.05 | 0.70 | 0.70 | 1.08 |
| TP | QC sample L | 1.50 | 0.15 | 0.54 | 0.50 | 0.50 | 1.75 |
| | QC sample M | 1.50 | 0.15 | 0.38 | 0.50 | 0.50 | 1.71 |
| | QC sample H | 1.50 | 0.15 | 0.19 | 0.50 | 0.50 | 1.68 |
| T-Cho | QC sample L | 1.50 | 0.20 | 0.37 | 0.50 | 0.50 | 1.71 |
| | QC sample M | 1.50 | 0.20 | 0.08 | 0.50 | 0.50 | 1.67 |
| | QC sample H | 1.50 | 0.20 | 0.04 | 0.50 | 0.50 | 1.67 |

As above, the obtained uncertainty estimates for ALT, LD, TP, and T-Cho of the QC sample L were 6.10%, 1.48%, 1.75%, and 1.71%, respectively. In the case of the QC sample M, the obtained uncertainty estimates were 1.27% for ALT, 1.09% for LD, 1.71% for TP, and 1.67% for T-Cho. In the case of the QC sample H, the obtained uncertainty estimates were 1.16% for ALT, 1.08% for LD, 1.68% for TP, and 1.67% for T-Cho.

The actual reproducibility (coefficients of variation CV) obtained by the measurement of the QC sample L were 5.4% for ALT, 1.3% for LD, 3.5% for TP, and 3.8% for T-Cho. In the case of the QC sample M, the obtained reproducibility were 1.0% for ALT, 0.9% for LD, 3.5% for TP, and 3.3% for T-Cho. In the case of the QC sample H, the obtained reproducibility were 1.3% for ALT, 1.2% for LD, 3.6% for TP, and 3.5% for T-Cho. When the uncertainties obtained from the QC measurement results were compared with the combined uncertainty estimates, all the three QC samples L, M, and H had poor reproducibility in TP and T-Cho, which are subject to the precision of the sample dispenser. When all the three QC samples have greater uncertainties in two analysis items, the cause can be attributed not to the reagent and samples but to the device-side. Further, since only those items that are subject to the uncertainty in the sample dispenser had greater uncertainties, it can be determined that some abnormality occurred in the sample dispenser.

Measurement Example 2

The following are other possible results that would be obtained when QC sample measurement is performed under the same conditions of Measurement Example 1. If uncertainty fluctuates in those items that are subject to the uncertainty in the sample dispenser, the magnitude of the fluctuation would be greater in the QC sample L of a low concentration due to larger noise influence. On the other hand, if uncertainty fluctuates in particular items regardless of whether they are items subject to the precision of the sample dispenser and the optical system, the cause can be attributed not to an abnormality of the analyzer but to the reagent or samples.

Embodiment 2

While Embodiment 1 has shown a specific example of data in which some uncertainties exceed reference values, it is preferred to measure, of all the items listed in Table 1, two or more items that are subject to the influence of the optical system and two or more items that are subject to the influence of the sample dispenser. Table 4 below shows how to classify the data whose uncertainty values exceed reference values when multiple optical-system-susceptible items (OS-susceptible items) and multiple sample-dispenser-susceptible items (SD-susceptible items) are measured. As in Patterns 1 and 2, when a single OS-susceptible item or a single SD-susceptible item exceeds a reference value, the cause can be attributed to the reagent used for the measurement. As in Pattern 3, when multiple OS-susceptible items exceed reference values, it can be determined that the optical system is abnormal. When multiple SD-susceptible items exceed reference values as in Pattern 4, it can be determined that the sample dispenser is abnormal. In Pattern 5, where a single OS-susceptible item and a single SD-susceptible item exceed reference values, the cause can be attributed to the reagent(s) used for the items. In Pattern 6, it is first determined that the optical system is abnormal because multiple OS-susceptible items exceed reference values. In addition, because a single SD-susceptible item exceeds a reference value, the cause can also be attributed to the reagent(s) used for the items. Conversely, in Pattern 7, where multiple SD-susceptible items and a single OS-susceptible item exceed reference values, the sample dispenser is highly likely to be abnormal. It is also possible that the reagent used for the OS-susceptible item may be abnormal. As in Pattern 8, when multiple (or all the) SD-susceptible items and multiple (or all the) OS-susceptible items exceed reference values, the cause can be attributed not to the components of the analyzer but to the control material or QC sample that was common to those items. As above, the cause of an abnormality can be attributed to particular components of the analyzer or stems from particular items. The use of more QC samples of varied concentrations would lead to greater accuracy in identifying abnormality causes.

TABLE 4

Data classification and possible causes

| | Influential factor | | |
|---|---|---|---|
| Data classification | Optical system | Sample dispenser | Possible abnormality cause |
| | Number of items that exceed reference values | | |
| Pattern 1 | Single | None | Reagent used |
| Pattern 2 | None | Single | Reagent used |
| Pattern 3 | Multiple | None | Optical system |
| Pattern 4 | None | Multiple | Sample dispenser |

TABLE 4-continued

Data classification and possible causes

| | Influential factor | | |
|---|---|---|---|
| Data classification | Optical system | Sample dispenser | Possible abnormality cause |
| | Number of items that exceed reference values | | |
| Pattern 5 | Single | Single | Reagent used |
| Pattern 6 | Multiple | Single | Optical system & reagent used |
| Pattern 7 | Single | Multiple | Sample dispenser & reagent used |
| Pattern 8 | Multiple | Multiple | QC sample |

When the cause of an abnormality is identified, an alert message to the effect that control data is abnormal is displayed on a screen such as the one illustrated in FIG. 8, with an alert sound. If there are multiple possible abnormality causes, all of them are notified. It is preferred that, as shown in Table 5 below, an alert message not only notify the cause(s) of an abnormality but also how to rectify the abnormality.

TABLE 5

Notification of possible abnormality causes

| | Possible cause | Alert message |
|---|---|---|
| 1 | Reagent used | A reagent abnormality has been found. Replace the reagent used for the analysis items that exceeded the reference values. |
| 2 | Optical system | An abnormality has been found in the optical system. Replace the lamp. |
| 3 | Sample dispenser | An abnormality has been found in the sample dispenser. Rinse or replace the sample probe. |
| 4 | QC sample | An abnormality has been found in the QC sample. Replace the sample. |

Embodiment 3

As another embodiment, it is also possible to judge reproducibility using the uncertainty judgment method of Embodiment 1.

DESCRIPTION OF REFERENCE NUMERALS

101: Data detector
102: Storage unit
103: Calculator
104: Display unit
105: Operating device
106: Judgment unit
201: Vertical axis of QC graph (CV value)
202: Horizontal axis of QC graph (date)
203: Plotted line for QC sample H
204: Plotted line for QC sample M
205: Plotted line for QC sample L
206: Combined uncertainty estimate

The invention claimed is:
1. An automatic analyzer, comprising:
a plurality of analyzer components, including:
an optical system including a light source,
a reagent dispenser to dispense a reagent, and
a sample dispenser, including a sample probe, to dispense a plurality of quality control (QC) samples;
a detector that outputs sample measurement data;
a storage unit that stores the sample measurement data and uncertainty data for the plurality of analyzer components;
a calculator that calculates an estimated combined uncertainty for each of a plurality of analysis items based on the uncertainty data, and calculates a measured combined uncertainty for each of the plurality of analysis items based on QC sample measurement data;
a judgment unit that detects analyzer component abnormalities by:
comparing the measured combined uncertainty with the estimated combined uncertainty for each analysis item, and,
when the measured combined uncertainty exceeds the estimated combined uncertainty for a particular analysis item, identifying an abnormality associated with one of the plurality of analyzer components; and
a display unit to display the abnormality,
wherein, after the display unit displays the abnormality, the analyzer component associated with the identified abnormality is replaced, including:
replacing the light source when the identified abnormality is an optical system abnormality,
replacing the reagent when the identified abnormality is a reagent abnormality,
replacing the sample probe when the identified abnormality is a sample dispenser abnormality, or
replacing the QC sample when the identified abnormality is a QC sample abnormality.
2. The automatic analyzer of claim 1, wherein the plurality of analyzer components further includes a rinser and a stirrer.
3. The automatic analyzer of claim 1, wherein the calculator calculates a standard deviation and a coefficient of variation for the QC sample measurement data.
4. The automatic analyzer of claim 1, wherein the plurality of QC samples, having a plurality of different concentration levels, are prepared and tested for each analysis item.
5. The automatic analyzer of claim 1, wherein the calculation of the estimated combined uncertainty for each analysis item is also based on calibration data for the plurality of analyzer components and analysis item parameters.
6. The automatic analyzer of claim 1, wherein the storage unit stores performance data for the plurality of analyzer components and analysis item parameters obtained from calibration measurements.
7. The automatic analyzer of claim 1, wherein the storage unit stores the calculated data.
8. The automatic analyzer of claim 1, wherein the uncertainty data are input to the computer.
9. The automatic analyzer of claim 1, wherein the judgment unit evaluates analysis items known to be subject to an influence of a particular analyzer component to examine whether the particular analyzer component is abnormal.

* * * * *